United States Patent
Naidu et al.

(10) Patent No.: US 11,504,500 B2
(45) Date of Patent: Nov. 22, 2022

(54) REDUCED DEAD SPACE CATHETER ADAPTER

(71) Applicant: Becton, Dickinson and Company, Franklin Lakes, NJ (US)

(72) Inventors: Jithendra Kumar Sathyanarayana Naidu, Singapore (SG); Zhee Min Jimmy Yong, Singapore (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 55 days.

(21) Appl. No.: 16/732,787

(22) Filed: Jan. 2, 2020

(65) Prior Publication Data

US 2020/0222662 A1 Jul. 16, 2020

Related U.S. Application Data

(60) Provisional application No. 62/792,252, filed on Jan. 14, 2019.

(51) Int. Cl.
*A61M 25/00* (2006.01)
*A61M 25/06* (2006.01)
*A61M 39/10* (2006.01)

(52) U.S. Cl.
CPC .... *A61M 25/0097* (2013.01); *A61M 25/0606* (2013.01); *A61M 39/105* (2013.01); *A61M 2039/1077* (2013.01)

(58) Field of Classification Search
CPC ............ A61M 25/0097; A61M 39/105; A61M 25/0606; A61M 2039/1077; A61M 39/06; A61M 39/04; A61M 2039/06; A61M 2039/0626; A61M 2039/066
See application file for complete search history.

(56) References Cited

U.S. PATENT DOCUMENTS

| 5,755,702 A * | 5/1998 | Hillstead et al. . A61M 25/0662 604/264 |
| 5,810,780 A * | 9/1998 | Brimhall et al. . A61M 39/0606 604/272 |
| 2004/0073159 A1 | 4/2004 | Nelson |
| 2016/0089529 A1* | 3/2016 | Bolz et al. ............ A61M 39/10 285/119 |

(Continued)

FOREIGN PATENT DOCUMENTS

| AU | 2013232371 | 9/2014 |
| CN | 202036618 | 11/2011 |

(Continued)

*Primary Examiner* — Rebecca E Eisenberg
*Assistant Examiner* — Anna E Goldberg-Richmeier
(74) *Attorney, Agent, or Firm* — Kirton McConkie; Whitney Blair; Kevin Stinger

(57) ABSTRACT

A catheter assembly may include a catheter adapter, which may include a distal end, a proximal end, a lumen extending between the distal end and the proximal end, and a side port. A septum may be disposed within the lumen of the catheter assembly. The side port may include a lumen in fluid communication with the lumen of the catheter adapter. The lumen of the side port may be distally-facing, which may facilitate flushing of fluid trapped proximate a distal face of the septum. The catheter assembly may include a catheter secured within the catheter adapter and extending distally from the catheter adapter.

5 Claims, 4 Drawing Sheets

(56) References Cited

U.S. PATENT DOCUMENTS

2017/0319822 A1   11/2017   Ang

FOREIGN PATENT DOCUMENTS

| CN | 204815139 | 12/2015 | | |
|---|---|---|---|---|
| EP | 0938871 | 9/1999 | | |
| WO | 2016/036468 | 3/2016 | | |
| WO | WO 2016036468 A1 * | 3/2016 | ............ | A61M 39/06 |

* cited by examiner

REDUCED DEAD SPACE CATHETER ADAPTER

RELATED APPLICATIONS

This application claims the benefit of U.S. Provisional Application No. 62/792,252, filed Jan. 14, 2019, and entitled REDUCED DEAD SPACE CATHETER ADAPTER, which is incorporated herein in its entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous catheter ("PIVC"). As its name implies, the over-the-needle PIVC may be mounted over an introducer needle having a sharp distal tip. The PIVC and the introducer needle may be assembled so that the distal tip of the introducer needle extends beyond the distal tip of the PIVC with the bevel of the needle facing up away from skin of the patient. The PIVC and introducer needle are generally inserted at a shallow angle through the skin into vasculature of the patient.

In order to verify proper placement of the introducer needle and/or the PIVC in the vein, a user generally confirms that there is "flashback" of blood in a flashback chamber of a PIVC assembly. Once placement of the needle has been confirmed, a user may temporarily occlude flow in the vein and remove the introducer needle, leaving the PIVC in place within the vein. The PIVC may then be used for fluid infusion and/or blood withdrawal or collection.

In some instances, during fluid infusion or blood collection, fluid may flow through the PIVC assembly in a non-laminar manner such that fluid is separated or becomes stagnant in some places and turbulent in others. These discontinuities can lead to fluid accumulation and bacteria within the PIVC assembly and may lead to removal and replacement of the PIVC inserted into the vasculature of the patient. Systems and methods described in the present disclosure can mitigate and/or overcome these drawbacks.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to catheter assemblies and related devices and methods. In some embodiments, a catheter assembly may include a catheter adapter, which may include a distal end, a proximal end, a lumen extending between the distal end and the proximal end, and a side port. In some embodiments, a septum may be disposed within the lumen of the catheter assembly. In some embodiments, the side port may include a lumen in fluid communication with the lumen of the catheter adapter.

In some embodiments, the lumen of the side port may be distally-facing, which may facilitate flushing of fluid trapped proximate a distal face of the septum. In these and other embodiments, the lumen of the side port may be disposed at less than 45° or at about 45° with respect to a longitudinal axis of the catheter assembly.

In some embodiments, the catheter assembly may include a catheter secured within the catheter adapter and extending distally from the catheter adapter. In some embodiments, the catheter may include a PIVC. In some embodiments, the catheter assembly may include an extension tube, which may include a first end integrated with the side port. In some embodiments, a connector may be disposed at a second end of the extension tube. In some embodiments, the catheter assembly may include a needle hub and an introducer needle extending from the needle hub. In some embodiments, the needle hub may be coupled to the proximal end of the catheter adapter.

In some embodiments, the side port may be proximally-facing. In some embodiments, the catheter adapter may include a deflector that may be configured to direct fluid flowing into the lumen of the catheter adapter from the side port towards the septum. In some embodiments, the deflector may include a protrusion. In some embodiments, the protrusion may include a face proximate the lumen of the side port that is sloped outwardly toward a middle of the lumen of the side port. In some embodiments, the face may be curved or planar.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1A:
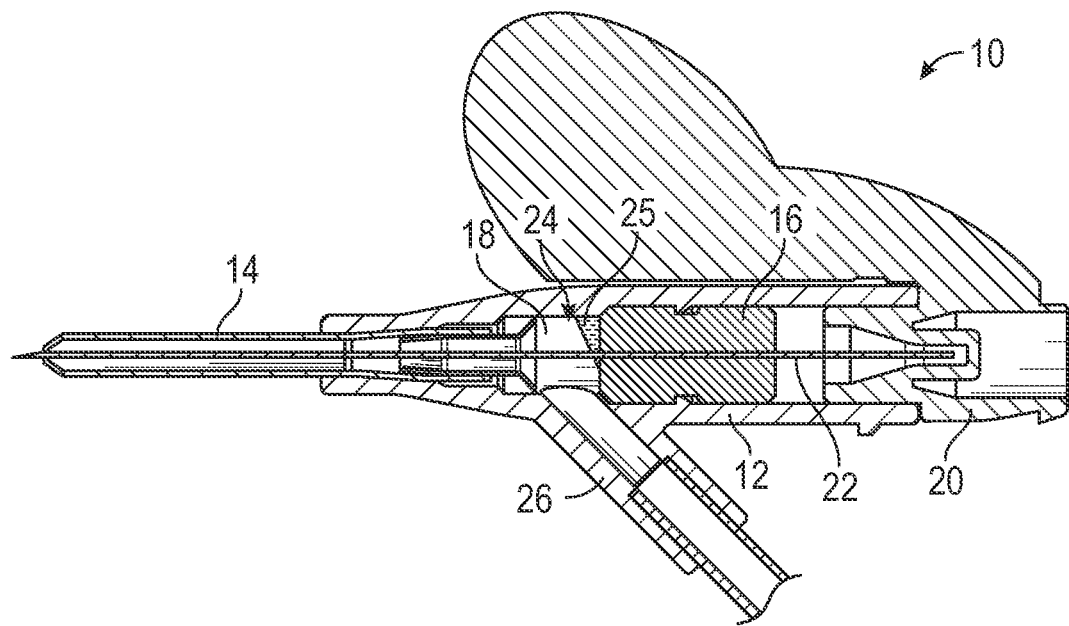
FIG. 1A is a cross-sectional view of a prior art catheter assembly, illustrating the prior art catheter assembly in an insertion position.
Figure 1B:
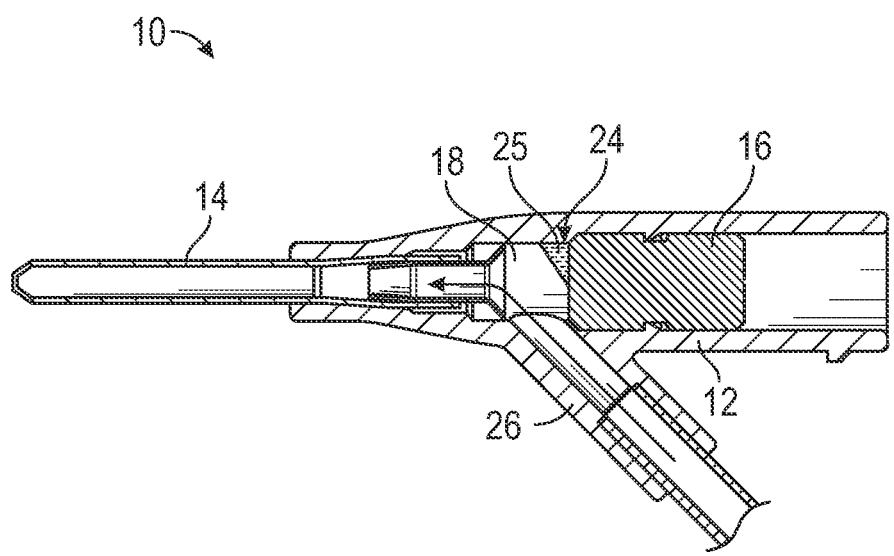
FIG. 1B is another cross-sectional view of the prior art catheter assembly of FIG. 1A, illustrating the prior art catheter assembly during flushing, according to some embodiments.

The present disclosure relates generally to catheter assemblies and related devices and methods. Referring now to FIGS. 1A-1B, a prior art catheter assembly 10 includes a catheter adapter 12 and a catheter 14 extending distally from the catheter adapter 12. A septum 16 is disposed in a lumen 18 of the catheter adapter 12. The prior art catheter assembly 10 includes a needle hub 20 and introducer needle 22, which extend through the septum 16 and beyond a distal tip of the catheter 14 when the prior art catheter assembly 10 is in an insertion position for insertion into vasculature of a patient, as illustrated in FIG. 1A.

The prior art catheter assembly 10 includes a dead space 24 within the lumen 18 of the catheter adapter 12. As used in the present disclosure, the term "dead space" is a broad term and is used in accordance with its ordinary meaning to refer to an unwanted or unproductive area that does not allow efficient and/or smooth fluid flow. As illustrated in FIG. 1B, fluid 25, which may include blood or another fluid, may get caught in the dead space 24. The fluid 25 may form eddy currents, turbulence, or stagnation in the dead space 24.

The fluid 25 may get caught in the dead space 24 in response to one or more of the following: insertion of the introducer needle 22 into the vasculature of the patient, withdrawal of the introducer needle 22 from the vasculature of the patient and proximally through the septum 16, fluid infusion through a side port 26, and blood collection through the side port 26. The dead space 24 may include a corner formed by the catheter adapter 12 and a distal face of the septum 16. The dead space 24 may be proximate the distal face of the septum 16.

Figure 2A:
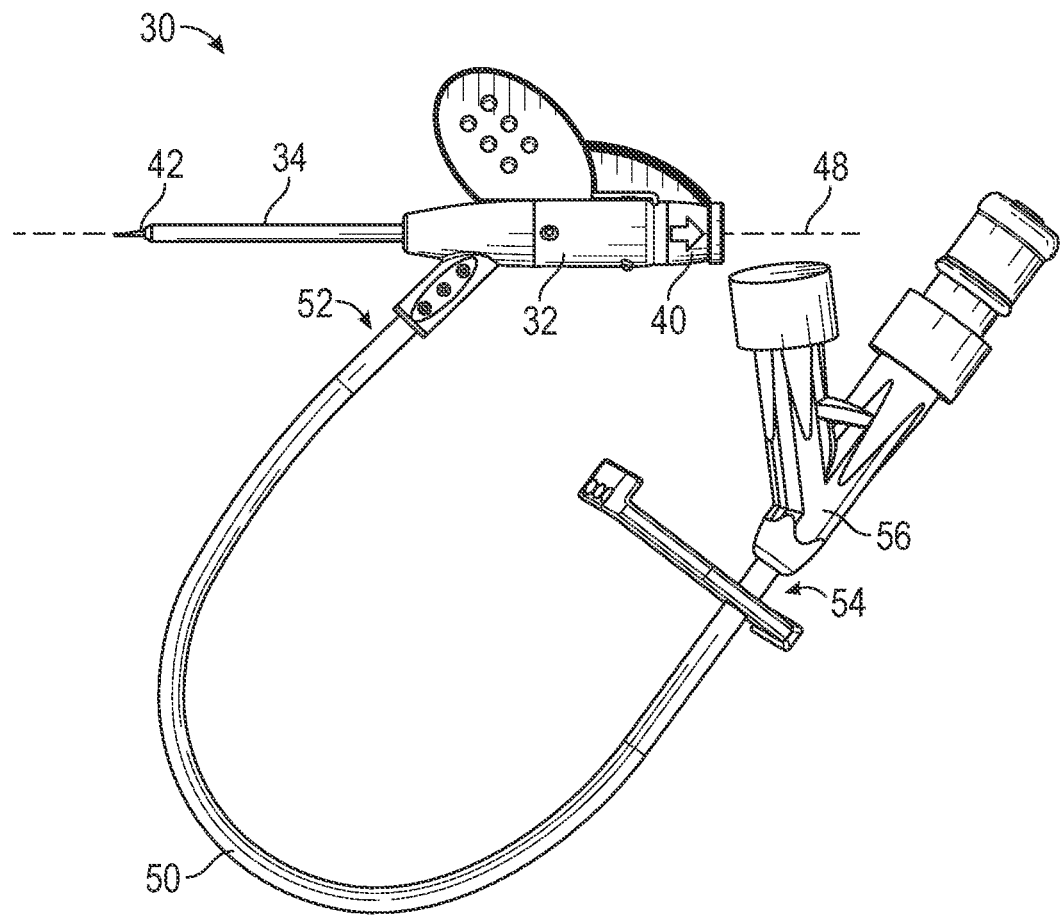
FIG. 2A is an upper perspective view of another catheter assembly, according to some embodiments.
Figure 2B:
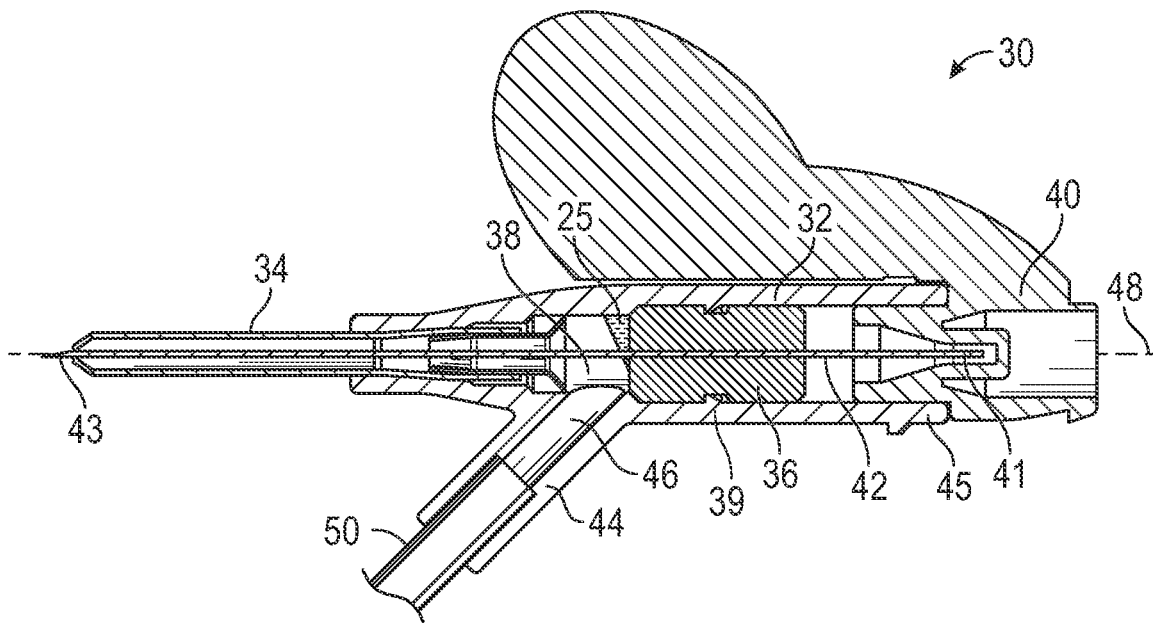
FIG. 2B is a cross-sectional view of the catheter assembly of FIG. 2A, illustrating the catheter assembly in an insertion position, according to some embodiments.
Figure 2C:
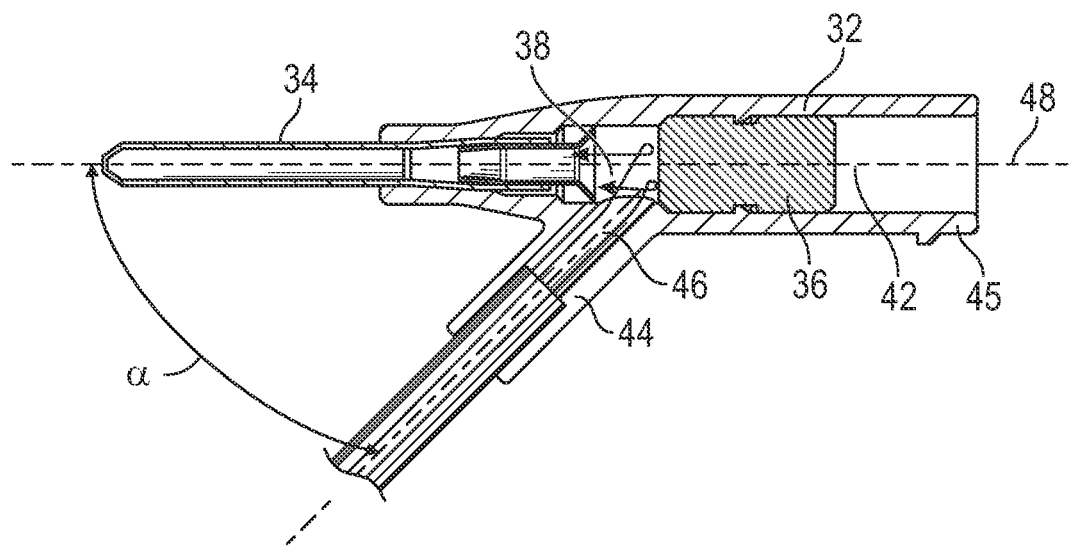
FIG. 2C is another cross-sectional view of the catheter assembly of FIG. 2A, illustrating the catheter assembly of FIG. 2A during flushing, according to some embodiments.

Referring now to FIGS. 2A-2C, a catheter assembly 30 is illustrated, according to some embodiments. In some embodiments, the catheter assembly 30 may include or correspond to the prior art catheter assembly 10. In further detail, in some embodiments, the catheter assembly 30 may include one or more features of the prior art catheter assembly 10. In some embodiments, the catheter assembly 30 may include may include a catheter adapter 32 and a catheter 34 extending distally from the catheter adapter 32. In some embodiments, a septum 36 may be disposed in a lumen 38 of a body 39 of the catheter adapter 32.

In some embodiments, the catheter assembly 30 may include a needle hub 40 and introducer needle 42, which may extend through the septum 36 and beyond a distal tip of the catheter 34 when the catheter assembly 30 is in an insertion position for insertion into the vasculature of the patient, as illustrated in FIGS. 2A-2B. In some embodiments, a proximal end 41 of the introducer needle 42 may be secured within the needle hub 40. In some embodiments, the introducer needle 42 may include a sharp distal tip 43. In some embodiments, the needle hub 40 may be removably coupled to the proximal end 45 of the catheter adapter 32 and removed as illustrated, for example, in FIG. 2C.

In some embodiments, a side port 44 may include a lumen 46 in fluid communication with the lumen 38 of a body 39 of the catheter adapter 32. In some embodiments, unlike the prior art catheter assembly 10, the lumen 46 of the side port 44 may be distally-facing, which may facilitate flushing of the fluid 25 via the side port 44 and reduce or eliminate the dead space 24 (illustrated, for example, in FIGS. 1A-1B). In some embodiments, infusion of fluid through the side port 44, as illustrated, for example, in FIG. 2C, may clear the fluid 25 disposed in the corner or angled area formed by the catheter adapter 12 and a distal face of the septum 16, which may prevent bacteria growth and infection.

In some embodiments, the lumen 46 of the side port 44 may be disposed at an angle α with respect to a longitudinal axis 48 of the catheter assembly 30. In some embodiments, α may be less than 45°. In some embodiments, α may be about 45°. In some embodiments, the body 39 of the catheter adapter 32 and the lumen 38 may be generally straight and aligned with the longitudinal axis 48. In some embodiments, the catheter 34 may include a PIVC. In some embodiments, the catheter assembly 30 may include a closed IV catheter assembly, such as, for example, the Becton Dickinson NEXIVA™ Closed IV Catheter System or the Becton Dickinson NEXIVA™ DIFFUSICS™ Closed IV Catheter System.

In some embodiments, the catheter assembly 30 may include an extension tube 50, which may include a first end 52 and a second end 54. In some embodiments, the catheter assembly 30 may include another type of catheter assembly, such as, for example, a non-integrated catheter assembly or a catheter assembly without the extension tube 50. In some embodiments, the first end 52 of the extension tube 50 may be connected or integrated with the side port 44. In some embodiments, a connector 56 may be disposed at the second end 54 of the extension tube 50.

In some embodiments, a configuration of the septum 36 may vary. In some embodiments, the septum 36 may include a one-piece septum or a multi-piece septum. In some embodiments, the septum 36 may include a low-drag septum. In some embodiments, the septum 36 may be constructed of an elastomeric or resilient material. In some embodiments, the septum 36 may seal the proximal end of the catheter adapter 32.

Figure 3A:
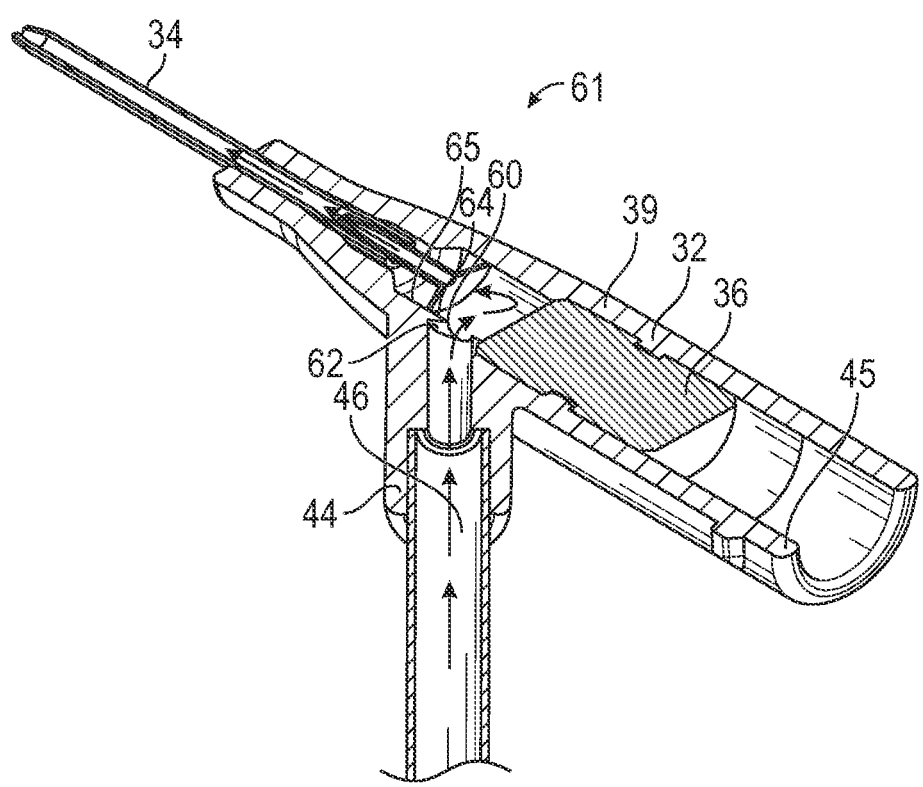
FIG. 3A is a cross-sectional view of another catheter assembly, illustrating an example deflector, according to some embodiments.

Referring now to FIG. 3A, in some embodiments, a catheter assembly 61 may include the side port 44, which may be proximally-facing. In these and other embodiments, the catheter adapter 32 may include a deflector configured to direct fluid flowing into the lumen 38 of the body 39 of the catheter adapter 32 from the side port 44 toward the septum 36, which may be disposed proximal to the lumen 46 of the side port 44. In some embodiments, the deflector may include a protrusion 60. In some embodiments, the catheter assembly 61 may include or correspond to the prior art catheter assembly 10 and/or the catheter assembly 30 illustrated in FIGS. 2A-2C.

In some embodiments, the protrusion 60 may include a first face 62 proximate the lumen 46 of the side port 44. In some embodiments, the first face 62 may be curved, as illustrated, for example, in FIG. 3A, or planar. In some embodiments, the first face 62 may be sloped and extend outwardly into the lumen 46. In some embodiments, a second face 64 of the protrusion 60 may be proximate the lumen 38 of the body 39 of catheter adapter 32. In some embodiments, the second face 64 may be flush with an inner wall 65 of the body 39 of the catheter adapter 32. In some embodiments, the first face 62 and the second face 64 may meet to form the protrusion 60. In some embodiments, the deflector may facilitate movement of the fluid 25 to prevent a dead space, such as the dead space 24 illustrated in FIGS. 1A-1B.

Figure 3B:
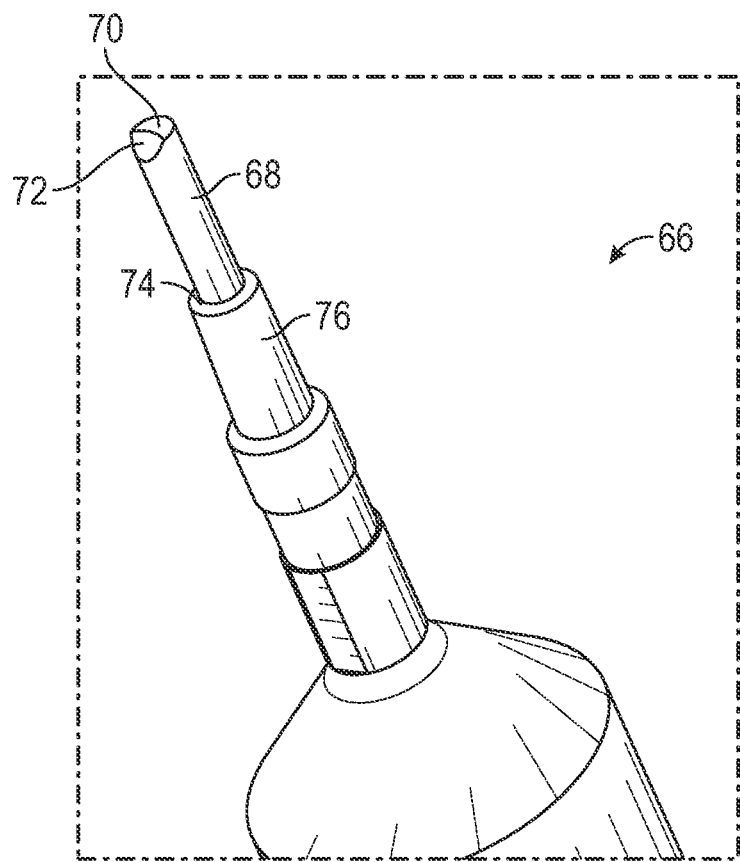
FIG. 3B is an upper perspective view of an example core pin that may be used to mold a side port of the catheter assembly of FIG. 3A, according to some embodiments.

Referring now to FIG. 3B, an example core pin 66 is illustrated, according to some embodiments. In some embodiments, the core pin 66 may be used to mold the side port 44 illustrated in FIG. 3A. In some embodiments, the core pin 66 may include a generally cylindrical end portion 68. In some embodiments, the generally cylindrical end portion 68 may include an end face 70 and a cut away 72 proximate the end face 70. In some embodiments, the cut away 72 may be planar or curved. In some embodiments, the end face 70 may be generally planar and/or perpendicular to a longitudinal axis of the core pin 66. In some embodiments, a step 74 may be disposed proximate the generally cylindrical end portion 68 and between the generally cylindrical end portion 68 and another generally cylindrical portion 76.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A catheter assembly, comprising: a catheter adapter having a distal end, a proximal end, a lumen extending between the distal end and the proximal end, and a side port, the side port having a lumen in fluid communication with the lumen of the catheter adapter, wherein the side port extends from the catheter adapter in a distal direction, wherein the lumen of the catheter adapter is permanently axially fixed with respect to a longitudinal axis of the catheter adapter; a catheter secured within the catheter adapter and extending distally from the catheter adapter; and a septum disposed within the lumen of the catheter adapter, wherein a central axis of the lumen of the side port intersects a distal face of the septum.

2. The catheter assembly of claim 1, further comprising an extension tube having a distal end integrated with the side port.

3. The catheter assembly of claim 2, further comprising a connector disposed at a proximal end of the extension tube.

4. The catheter assembly of claim 1, wherein the side port extends in the distal direction at about 45° with respect to a longitudinal axis of the catheter assembly.

5. The catheter assembly of claim 1, further comprising a needle hub and an introducer needle extending from the needle hub, wherein the needle hub is coupled to the proximal end of the catheter adapter.

* * * * *